United States Patent [19]

Shamos

[11] Patent Number: 5,193,855
[45] Date of Patent: * Mar. 16, 1993

[54] PATIENT AND HEALTHCARE PROVIDER IDENTIFICATION SYSTEM

[76] Inventor: Morris H. Shamos, 3515 Henry Hudson Pky., Bronx, N.Y. 10463

[*] Notice: The portion of the term of this patent subsequent to Dec. 10, 2008 has been disclaimed.

[21] Appl. No.: 530,222

[22] Filed: May 30, 1990

Related U.S. Application Data

[63] Continuation-in-part of Ser. No. 485,828, Feb. 27, 1990, Pat. No. 5,071,168, which is a continuation of Ser. No. 302,023, Jan. 25, 1989, abandoned.

[51] Int. Cl.$^5$ ............................................. B42D 15/00
[52] U.S. Cl. ...................................... 283/117; 382/2; 283/68; 283/78; 283/69; 283/900
[58] Field of Search ................ 283/68, 78, 69, 900, 283/117; 382/2, 4

[56] References Cited

U.S. PATENT DOCUMENTS

| | | | |
|---|---|---|---|
| 3,848,112 | 11/1974 | Weichselbaum | 235/61.7 R |
| 3,872,448 | 3/1975 | Mitchell, Jr. | 340/172.5 |
| 4,109,237 | 8/1978 | Hill | 340/146.3 |
| 4,121,574 | 10/1978 | Lester | 128/2.05 R |
| 4,476,381 | 10/1984 | Rubin | 235/375 |
| 4,983,036 | 1/1991 | Froelich | 382/4 |

FOREIGN PATENT DOCUMENTS

| | | |
|---|---|---|
| 821851 | 3/1975 | Belgium . |
| 904435 | 7/1986 | Belgium . |
| 0121222 | 10/1984 | European Pat. Off. . |
| 8434287 | 5/1986 | Fed. Rep. of Germany . |
| WO87/02160 | 4/1987 | PCT Int'l Appl. . |
| 2185937 | 8/1987 | United Kingdom . |

Primary Examiner—Paul A. Bell
Attorney, Agent, or Firm—Morgan & Finnegan

[57] ABSTRACT

The invention relates to a patient and healthcare provider identification system which includes a database of patient and healthcare provider information including the identity of each patient and provider and some identification criteria (such as fingerprint data); a print scanner for reading the print information from a patient or provider; a control system for matching the print data read by the scanner with the print data stored in memory; and a printer for printing labels or generating stamps or other visually perceptible medium for positively identifying the patient or provider and creating a record of the identification.

14 Claims, 7 Drawing Sheets

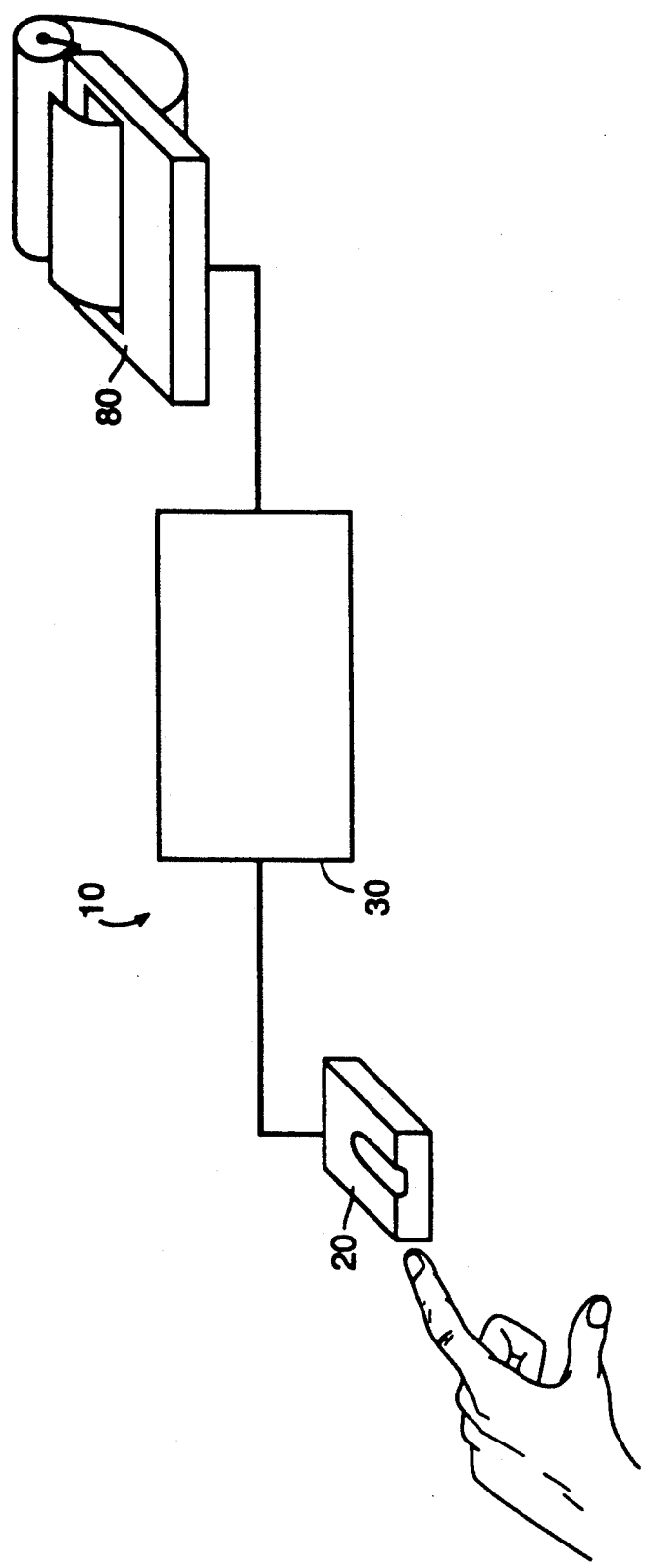

FIG. 5

BMHC TRANSFUSION REQUISITION: RED CELL PRODUCTS

– CURRENT T&S REQUIRED. NON-OR TX ARE PREPARED AT ISSUING: CALL BB 10 MINUTES BEFORE PICK UP

PATIENT
NAME _____
I.D. # _____

INDICATION (Check box, write in value)
☐ Anemia – Hgb or Hct: _____
☐ Blood Loss – Est. Amt: _____
☐ Blood Loss – B.P.: _____
☐ Repeated Phlebotomy (Neonatal Only)
☐ Intraoperative – Procedure: _____
☐ Standard Surgical Blood Order
☐ Other – Reason: _____
☐ Major Bleeding (BB will keep ahead on subsequent telephoned orders)

* ALL SECTIONS MUST BE COMPLETED *

Date/Time Ordered _____
Date/Time Required _____
Diagnosis _____

PRODUCT                    # UNITS
☐ Red Blood Cells _____
  ☐ Patient has had directed Donation(s)
  ☐ Patient has made Autologous Donation(s)
☐ Other: _____
  Reason: _____

ORDERING PHYSICIAN
Signature _____
PIN (I.D. #) _____
Beeper/Ext. # _____

BB-390

*REQUEST IS VALID FOR ONE ORDER ONLY*

Bar Code Identifying Transfusion Requisition

Supplied Automatically

PATIENT AND HEALTHCARE PROVIDER IDENTIFICATION SYSTEM

BACKGROUND OF THE INVENTION

This application is a continuation-in-part of co-pending U.S. patent application Ser. No. 07/485,828 filed Feb. 27, 1990, now U.S. Pat. No. 5,071,108 which is a continuation of U.S. patent application Ser. No. 07/302,023, filed (now abandoned).

The present invention relates to the field of patient and healthcare provider identification, and particularly to methods, devices and systems for confirming the identities of individuals receiving treatment and the individuals providing such treatment.

Disadvantages and risks resulting from misidentification of patients in the health care field are well-known, and in some instances may be life-threatening, as in surgery, drug or transfusion administration, emergency room trauma or cardiovascular intervention. U.S. patent application Ser. No. 07/302,023, by the inventor hereof, discloses methods and systems for confirming the identity of an individual to receive a procedure or treatment with the patient for whom said procedure or treatment is actually intended.

Systems and methods for positive identification of patients in hospitals and other institutions have been for many years the subject of ongoing efforts at improving reliability. Invariably, such patient identification systems prior to applicant's application Ser. No. 07/302,023 have relied upon some physical artifact such as a wrist bracelet or imprint card worn of carried by the patient, with the inevitable transcription and/or ownership errors to which these are subject, rather than on some unequivocal physical characteristic of the patient. Devices that produce labels from the patient's wristband have been developed to avoid transcription errors, but there are known instances where wristbands have been removed or exchanged by patients, and in any event such a system cannot be effectively used in outpatient clinics.

In contrast, the above-referenced patent application U.S. Ser. No. 07/302,023, which is incorporated herein by reference, provides the reliability of machine-readable correlation from the arrival of the patient for admission to the institution to the appearance of an individual for a treatment or procedure intended for that patient, whose identity can now be incontrovertibly confirmed immediately and at the actual site of treatment. This is achieved without the risks attendant to breaking the chain of computer-confirmation that can result from human interventions by potentially numerous workers who may be unskilled, unfamiliar with the patient in question, or both.

In the preferred embodiment of the system of U.S. Ser. No. 07/302,023, the hospital or other medical facility has at its admitting office, nursing station(s) and ancillary departments involved with patient diagnosis or treatment, a fingerprint storage assembly consisting of an optical fingerprint scanner, a computer/interface unit and a label printer. Optical fingerprint scanners, which scan and record by computer the principal features of the print of a finger placed upon its aperture, are available commercially for security applications (e.g., for access to secure areas or to computers). Likewise available commercially are label printers which produce an adhesive label containing information, including a bar code, supplied to it by a computer. Alternatively, a computer-driven stamping device may be used to print the desired patient (or other) information directly on a medical form or patient file record rather than on a label. Portable storage assemblies may be used at the patient bedside for procedures normally done at such a locale (e.g., drawing blood or other patient samples, infusion or transfusion therapy, medication administration, etc.).

Upon admission to the medical facility, in addition to the usual demographic and other information provided by the patient and recorded by computer, the patient's print characteristic (thumb or forefinger) is recorded and stored along with all other pertinent information on the patient through the computer/interface unit of the storage assembly. Such information may include the patient's name and a patient number assigned by the medical facility, the latter being both in numerical and machine-readable bar code format. Where the institution has a facility-wide information system, the pertinent patient information, such as name, number, bed location, admitting physician, etc., becomes immediately available at all terminals on the system. Where a facility-wide system is not available, the information can be distributed periodically to those departments having a need for it by means of floppy disks, from which the information can be downloaded to the departmental computer. From this point on, whenever a test or other medical procedure is to be performed on the patient, the patient's identification can be simply and positively checked by placing the same digit on a fingerprint scanner located in the department or service performing the procedure. In some ancillary locations, where patient samples rather than patients normally appear, as in the clinical laboratory or blood bank, bar code scanners coupled to the computer system may be employed to positively identify a given specimen or blood bag from the label affixed thereto.

The general use of identification materials for security or law enforcement purposes or credit cards bearing photographs or fingerprints has been the subject of earlier patents and commercially available products. Examples of such patents include, for example, McKee, et al., U.S. Pat. No. 3,709,524; Hollie, U.S. Pat. No. 2,712,514; Degruchy, U.S. Pat. No. 2,395,804; and Voght, U.S. Pat. No. 1,380,506. Commercial security systems including the use of fingerprint identification are available, for example, from Fingermatrix, Inc., North White Plains, N.Y.; Thumbscan, Inc., Oakbrook, Ill.; and Identix, Inc., Palo Alto, Calif.

Drexler, in U.S. Pat. No. 4,692,394, discloses a personal identification card on which are recorded visual images, such as a face image or fingerprint, and laser recorded data. By means of in situ laser recording, transaction data, information, or the like related to the photographic image is recorded at subsequent times. For example, insurance claims or medical record entries may be processed sequentially. A photograph of the claimant is alleged to protect against fraudulent use of the card.

Miller, et al., in U.S. Pat. No. 3,694,240, disclose an identification system in which an individual's fingerprint is taken at the time identification is to be made and compared to a fingerprint record in a master file of the person the individual purports to be. The prints are taken in the form of transparencies, and those of the master record and those taken at the time of identification are superimposed. The comparison is made by measuring the amount of light passing through the transparencies.

Estrada, in U.S. Pat. No. 4,325,570, discloses an identification system which utilizes an individual fingerprint and an identifier which can be correlated to the fingerprint and to a listing of valid identifiers. An identification card is used which has the individual's fingerprint, a grid superimposed over the fingerprint and an identifier printed thereon. The identifier is a series of symbols representing characteristics of the fingerprint. This allows the individuals to be identified with a three-point identification check by comparing a new fingerprint of the individual to the fingerprint on the card, comparing the fingerprint on the card to the identifier, and confirming that the identifier is valid by determining if it is included in a list of approved individuals.

Relating to hospital or patient care environments, a label printer which makes self-adhesive labels from an identification plate attached to a patient wristband is described in promotional literature from Bio-Logics Products, Inc., Salt Lake City, Utah and in U.S. Pat. No. 4,145,966.

Brown, in U.S. Pat. No. 4,632,428, discloses a medical data, identification and health insurance card which carries both visually and machine-readable data, including a photograph, and appears to be a compact source of a relatively complete medical history. Brown also cites other patents relating to medical data cards, including Calavetta, U.S. Pat. No. 3,921,318; Hanna, et al., U.S. Pat. No. 4,031,640; Domo, U.S. Pat. No. 4,236,332; and Anderson, et al., U.S. Pat. No. 4,318,554.

Siegel, in U.S. Pat. No. 4,730,849, discloses a device and system for the identification of medication in an attempt to assure that only the patient who is intended to be named on a medication container, in the form of a label, and/or patient record, such as a medication card or chart, is, in fact, named thereon. Alternatively, upon admission a patient may be issued a "non-removable" identifying wrist band having a machine-readable portion and, optionally, a computer-generated likeness or a miniature photograph of the patient. Before treatment, the coded information on the patient wristband can be compared with that introduced into computerized central records upon admission.

Notwithstanding the above mentioned earlier work, no known method or system exists for automatically and reliably identifying two related individuals in a hospital or clinical environment (such as patient and physician or mother and infant) and for linking these individuals through identification mediums.

It is, therefore, an object of the invention to provide a system and method for identifying related individuals in a hospital or clinical environment and for providing an identification record for such individuals.

SUMMARY OF THE INVENTION

These and other objects of the invention are met by providing a patient and healthcare provider identification system which includes a database of patient and healthcare provider information including the identity of each patient and provider and some identification criteria (such as fingerprint data); a fingerprint scanner for reading the fingerprint information from a patient or provider; a control system for matching the fingerprint data read by the scanner with the fingerprint data stored in memory; and a printer for printing labels or generating stamps or other visually perceptible medium for positively identifying the patient or provider and creating a record of the identification. Such generated labels or stamps can be applied to a chart or a drawn specimen, for example, as a record identifying the person providing the sample and the person drawing the sample or analyzing the sample. The control system can also provide additional security by checking a database to ensure that the provider is authorized by the hospital or clinic to perform an indicated treatment. The system can also be adapted to provide identification support linking other pairs of individuals, such as mother and child in a maternity unit.

BRIEF DESCRIPTION OF THE DRAWINGS

The invention will be described in greater detail by reference to the drawings in which:

FIG. 3 illustrates a further embodiment of the invention wherein a form-feeder is used and wherein patient and/or provider identification information are provided as part of a comprehensive form;

FIG. 5 illustrates an example of a form generated in the system of FIG. 3 or preprinted and subsequently stamped in the system of FIG. 4;

DETAILED DESCRIPTION OF THE DRAWINGS

Healthcare facilities, such as hospitals, clinics, nursing homes, etc., must not only establish a positive correlation between a given patient and an intended medical procedure for that patient (e.g., diagnostic tests, medications, therapies, surgery, etc.) but may also wish to identify (for medical, legal and/or administrative reasons) the individuals (physicians, nurses, etc.) responsible for ordering and administering such procedures. In some medical procedures, such as blood banking, transfusions, surgery, and obstetrics (for mother-newborn matching), complete audit trails may be mandatory. In others, such as laboratory testing, drug administration and radiology, audit trails can lead to better, more efficient patient management and minimize the incidence of serious medical errors.

The patient identification system of applicant's earlier U.S. patent application Ser. No. 07/302,023 (described earlier and incorporated herein by reference) may be modified as disclosed herein to include such provider information as well as patient information, thereby dissuading or preventing unauthorized personnel from instituting or carrying out medical procedures for which they are not qualified.

Figure 1:
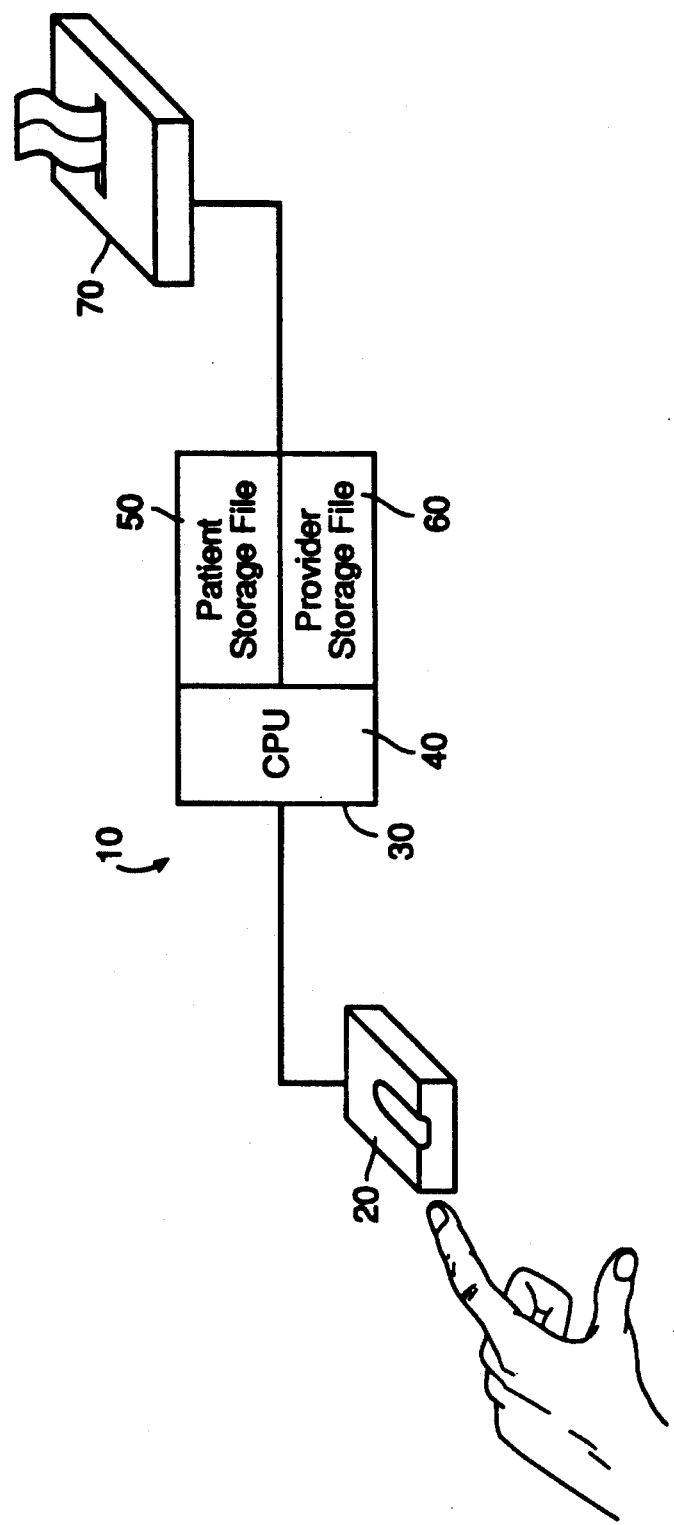
FIG. 1 is an illustration of an identification system according to the invention.

Referring to FIG. 1, which illustrates one embodiment of the invention, a fingerprint storage and identification system 10 is shown, having an optical fingerprint scanner 20, a computer/interface unit 30 which includes memory storage facility and a label printer 70. Computer/interface units and label printers are, of course, in wide usage and are generally adaptable to the present invention. Similarly, fingerprint scanners are well known and are commercially available, for example, from Fingermatrix, Inc., North White Plains, N.Y.; Thumbscan, Inc., Oakbrook, Ill; and Identix, Inc., Palo Alto, Calif.

Figure 7:
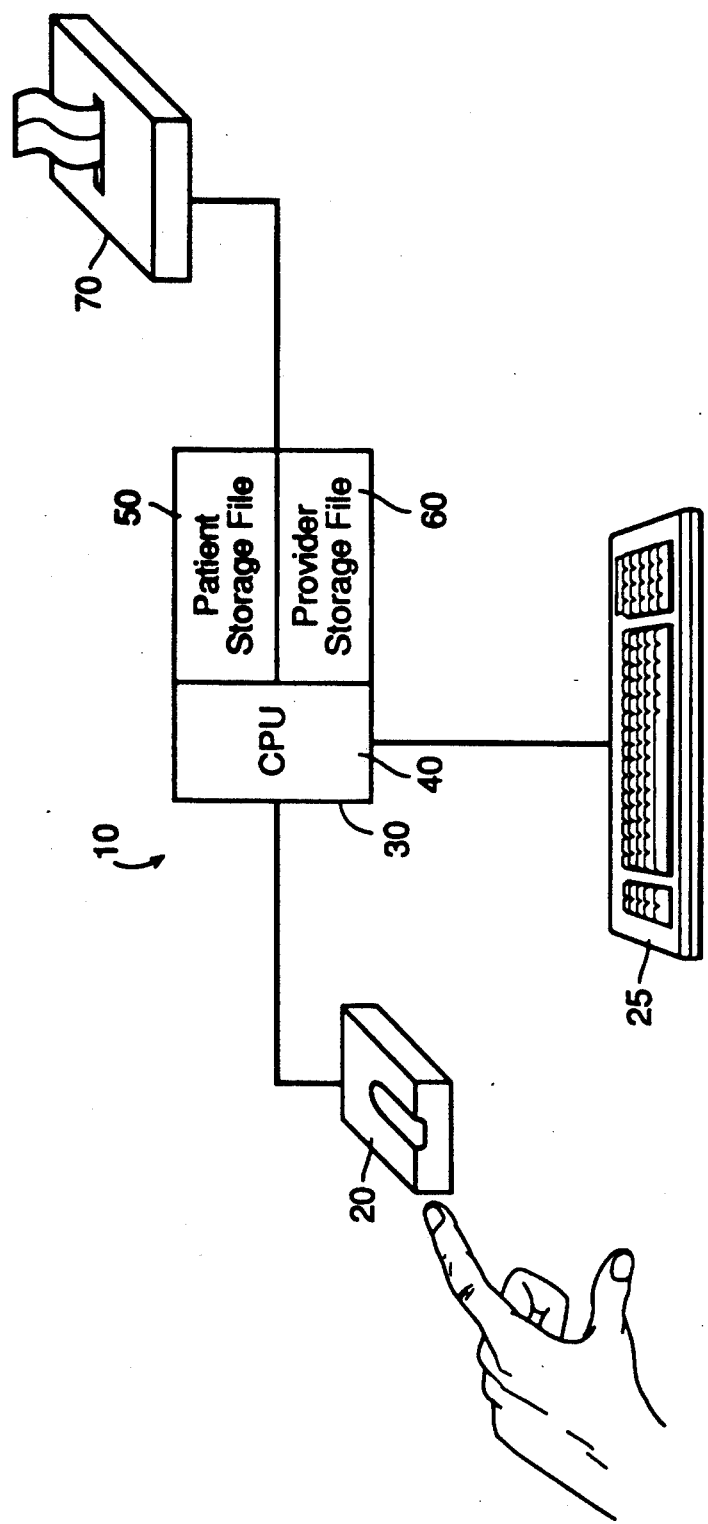
FIG. 7 is an illustration of the present invention showing an input keyboard.

Upon admission to the hospital, a patient's fingerprint is scanned and electronically encoded through known techniques. This data may be combined with other information associated with that patient, such as the patient's name, identification number, bed number, admitting physician and date of admission. This information is then stored in the hospital's computer system. Information relating to patients and healthcare providers is input into the system through a keyboard 25 (FIG. 7). Healthcare provider fingerprint data and identification information are also stored in the computer system. When a patient is to undergo a treatment or procedure, he places his finger upon the aperture of the fingerprint scanner 20, which scans the print and converts it to electronic form. The healthcare provider then repeats the procedure, giving his fingerprint. The electronically encoded prints are then transferred to the computer/interface unit 30.

The computer/interface unit 30 includes a central processing unit (CPU) 40 (FIG. 1) and memory facilities, including a patient data storage file 50 and a healthcare provider data storage file 60. Of course, one file can be maintained to store both patient and healthcare provider data. Upon receiving the electronically encoded patient and provider fingerprints, the CPU 40 compares the prints with the encoded prints located in the patient and provider storage files 50 and 60. A patient's identity is reliably established when a match for his scanned print is found in the patient storage file 50. The CPU 40 also determines the identity of the healthcare provider by matching his print with the print data located in the provider storage file 60. If the healthcare provider's print is not found in the provider storage file 60, the process terminates and no information is printed. Similarly, if the computer determines that the provider is not authorized to perform that particular treatment or procedure, the process terminates without printing the information. In both cases, an audible and/or visible alert may also be issued in the appropriate administrative office.

Figure 2A:
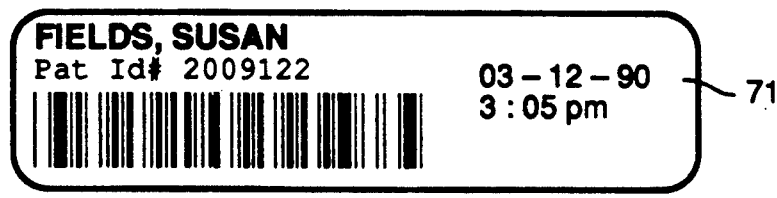
FIGS. 2A, 2B and 2C illustrate examples of patient and provider identification labels according to the invention.
Figure 2B:
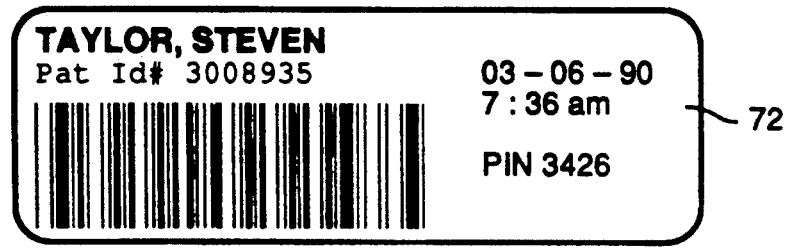
Figure 2C:

If a healthcare provider is authorized, the identification information is forwarded from the computer/interface unit 30 to a label printer 70, which prints the information on adhesive labels. These labels are then transferred to patient records, specimen containers, or as needed. FIGS. 2A-C identify three illustrative adhesive labels or stamps 71, 72 and 73. In one label embodiment 71, illustrated in FIG. 2A, only patient identification information (such as the name "FIELDS, SUSAN", the patient's identification number "2009122", and the date and time of admission "Mar. 12, 1990, 3:05 pm") are indicated. In another label embodiment 72, illustrated in FIG. 2B, both patient and provider information are indicated. The provider may be a physician, phlebotomist or other accredited healthcare provider (e.g., a nurse, technician, etc.). The healthcare provider number appears as a "PIN" number. In a third label embodiment 73, illustrated in FIG. 2C, only healthcare provider information is indicated. In all cases, patient information labels 71, patient/provider information labels 72 and provider information labels 73, label printer 70 prints the patient identification information in both visually readable and machine-readable bar code form.

In an alternative embodiment of the present invention, the identification information is printed by means of a form-feeder printer 80 (FIG. 3) of a type known to the art, which prints the information directly onto medical forms or patient records fed therethrough.

Figure 4:
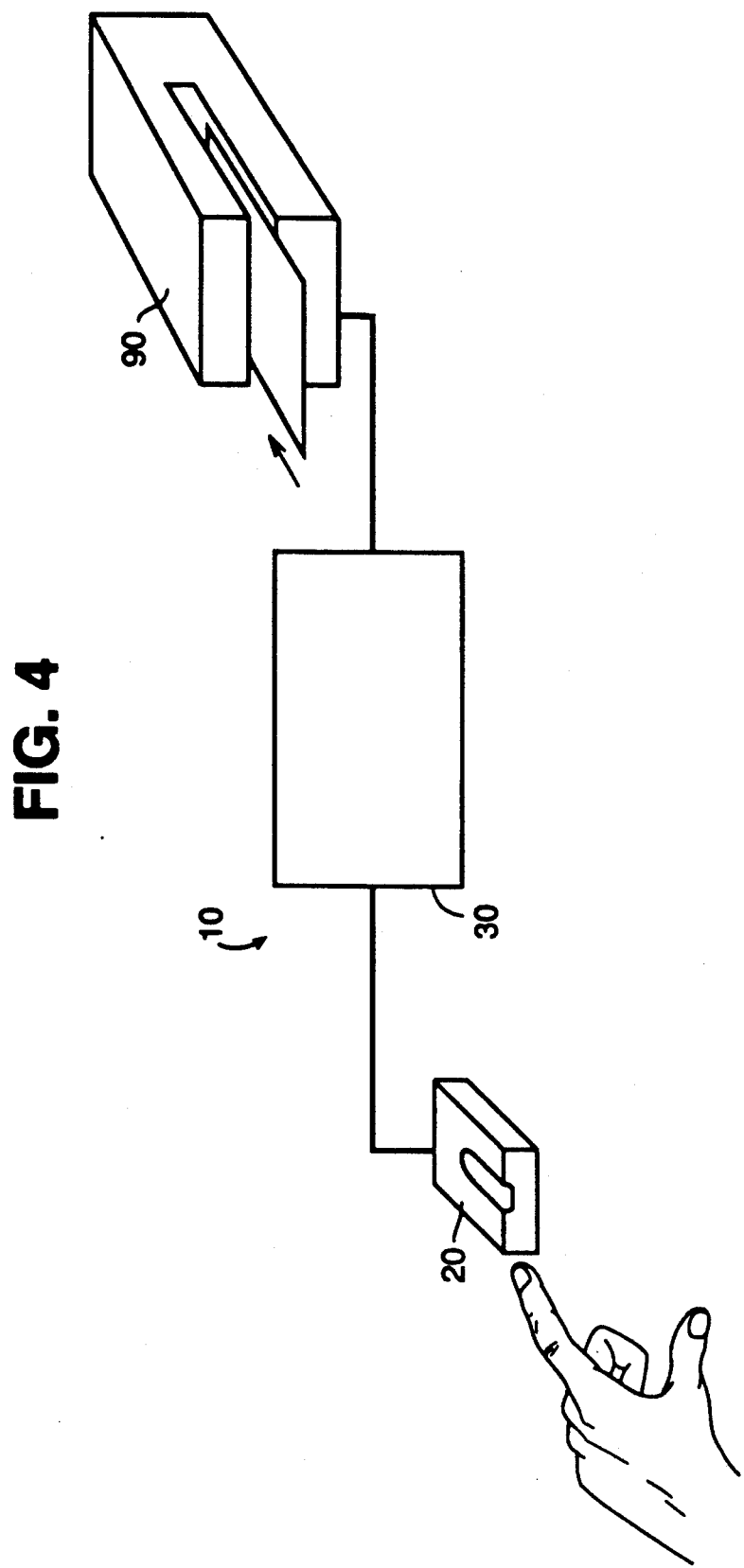
FIG. 4 illustrates an alternative embodiment of the present invention wherein a stamper is used to produce a visually perceptible record of patient and/or provider identification information.

In a further embodiment of the present invention, the identification information is printed by means of a stamper 90 (FIG. 4). The stamper 90 is actuated by insertion therein of a record medium such as a medical form or hospital record. Once actuated, the stamper 90 stamps patient and/or provider identification information directly onto the record medium so inserted.

Figure 6:
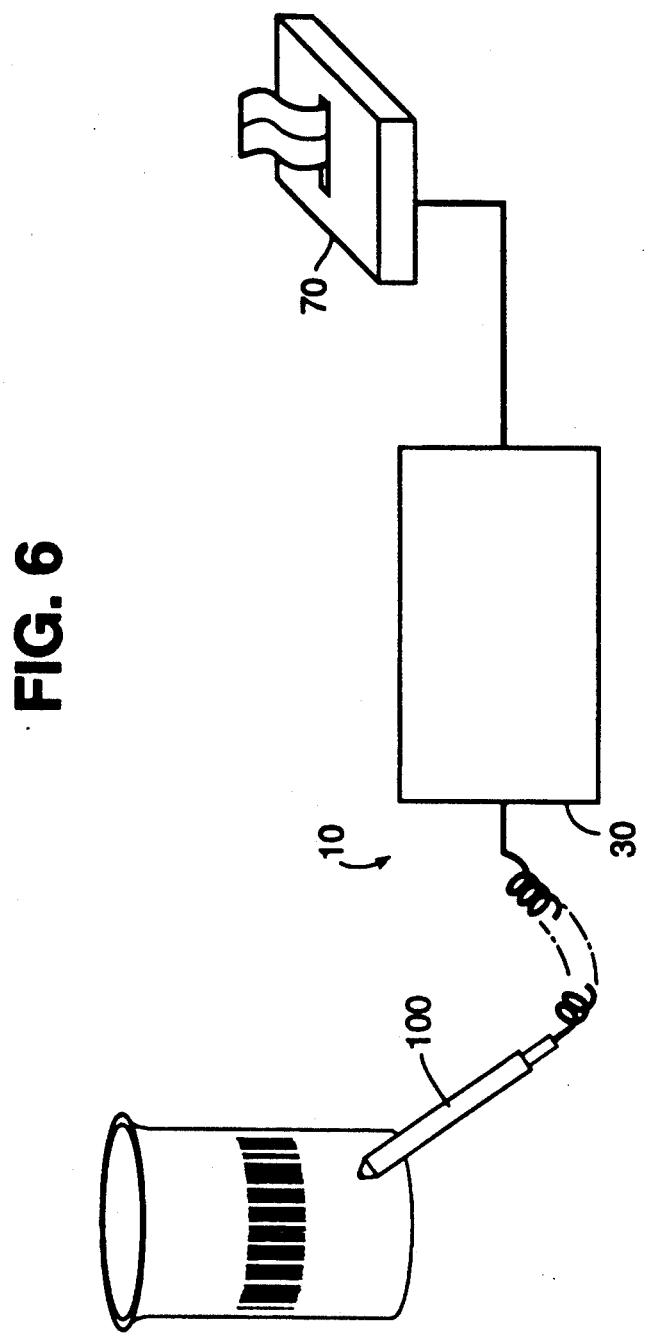
FIG. 6 illustrates a further embodiment wherein a machine-readable print scanner is employed to scan machine-readable bar codes.

In some ancillary locations, patient samples rather than the actual patients appear. FIG. 6 illustrates a further embodiment of the present invention, in which a machine-readable print scanner is employed to positively identify patient samples or specimens from the label affixed thereto. When a healthcare provider receives a patient sample or specimen, he or she scans the bar code On the attached label with a light pen 100, which converts the encoded identification information to electronic form. The electronically coded information is then transferred to the computer/interface unit 30 which confirms the identity of the patient as previously described. Alternatively, if the sample or specimen is to be assayed by an automated analyzer, the analyzer itself may be provided with a mechanism for automatically scanning the bar code on the container as it passes through the analyzer and entering the patient identification information into the computer.

The embodiment disclosed above utilizes a light pen scanning device for reading machine-readable print. However, the invention can also be adapted to apply any of a variety of known technologies for scanning machine-readable print. Examples include laser scanning, digital or analog analysis or holographic analysis.

Depending upon the medical procedure involved, and the rules established by the healthcare facility, several identification points may comprise a complete audit trail which may be used advantageously in accordance with the invention.

The first point is the individual (usually a physician) who orders the procedure. Written orders are normally required, signed by the physician, or, where permitted, by a suitably authorized intern, resident, nurse or physician's assistant. Frequently, the audit trail is broken at this point by an unauthorized individual who enters the order using the physician's name or initials. Even assuming good intentions on the part of this unauthorized individual and the physician who orally initiated the request, perhaps by telephone, there is the possibility of error; hence it is important to know who actually entered the order at the nursing station.

This may be accomplished in accordance with the present invention by installing a storage assembly at each nursing station and assigning to every authorized staff member an identification number (normally done in large healthcare establishments), as well as entering into the system the fingerprint identification of each staff member. Then, when an order is entered at a nursing station, the individual entering the order produces a label, such as that shown at items 72 and 73 in FIGS. 2B and 2C respectively, by placing the appropriate digit on the fingerprint scanner, which label is then affixed to the order form or patient record. A label produced in this manner and affixed to the order form or patient record is equivalent to the provider's signature thereon. For such uses, the label may or may not include patient identification information, as this information may already exist on the order form or patient record (see FIG. 2C).

Alternatively, the order form may be inserted into a stamper which prints the same information directly on the form when the scanner recognizes the fingerprint of the staff member.

Nursing notes or other entries on the patient record, instead of being signed or initialed by the individual making the entry, may be identified by labels or stamps generated in a like manner. Treatment cards, medication cards, etc., are routinely used in many healthcare establishments. Fixing the time of treatment or medication can be very important in some cases.

The advantage here is not only in having a positive identification of the individual responsible for making the entry, but also the date, time, location and any other desired information regarding that individual. The discipline imposed on the healthcare staff by the use of such a system can be an added advantage in the sense of improved medical practice and efficiency.

The above examples illustrate one application of the system, namely, to identify the healthcare individual entering an order or notes in a patient record, regardless of whether that individual is authorized to do so. Such a procedure may develop a measure of self-discipline among the staff in the institution but is not error-proof or tamper-proof.

For orders that may carry an element of risk, such as blood transfusions, infusion therapy or the administration of certain drugs, the system is easily modified to accept orders only from authorized individuals. This is accomplished by having a bar code on such order forms as described above, the bar code to be read by a combination reader-stamper when the form is inserted therein, the stamper operating only when an individual authorized to place such an order (see FIG. 2B) is so identified by the fingerprint scanner. The identification software may accordingly be coded to assign to each staff member the appropriate levels of authorization required for such procedures.

Another potentially weak link in the healthcare audit trail is in the actual performance of a given procedure, i.e., identifying the individuals who carry out certain orders and preventing unauthorized staff from performing such procedures. Several examples will serve to show how the system may be used for this purpose.

One example is in the drawing of blood samples at the bedside for testing in the laboratory. In the applicant's earlier application U.S. Ser. No. 07/302,023, adhesive labels were generated to identify the samples by having the patient activate the label printer via the fingerprint scanner. This represents a marked advance over any of the prior practices where: (a) the phlebotomist (physician, nurse or venipuncture technician) looks at the patent's wristband and writes the patent's I.D. number on a blank label on the sample tube; or (b) labels are prepared in advance in the laboratory from order forms prepared at the nursing stations and sent to the laboratory for carrying by the phlebotomist to the bedside, selected by comparison with the patient's wristband (or through oral interrogation of the patient) and affixed to the sample tube; or (c) labels are prepared mechanically at the bedside from embossed wristbands in much the same way that credit cards are used. It will be noted that all these methods rely upon the wristband as the primary source of information, with the problems attendant upon the use of such an artifact, and that the first two are subject to transcription errors as well.

In contrast, the present invention relies only upon an unequivocal physical characteristic of the patient, namely, a fingerprint. Through computer programming the system can be made to require two fingerprint I.D.'s, one being the patient and the other the phlebotomist and unless both are generated within a few minutes of one another, the label will not be printed. Likewise, unless the staff member is authorized to draw blood samples, a label will not be printed. When a label is printed for a blood sample or record, it will generally contain the information shown in FIG. 2B, identifying both the patient and the phlebotomist, and showing the date and time the blood was drawn.

In addition to generating labels, the system can be caused to retain information in memory for subsequent recall or statistical analysis. Moreover, beyond ensuring that the phlebotomist is properly authorized, the laboratory director or administrator may wish to know the identity of this individual for other purposes.

A similar procedure can be used for surgical patients to prevent incorrect surgery or even "ghost" surgery. A surgical order form is prepared by the surgeon in the presence of the patient, with both identities entered into the system through a fingerprint scanner. Also entered, via keyboard, is the name and/or code number of the proposed surgical procedure. The system will not accept a physician who has not been authorized by the institution to carry out the proposed procedure. The patient consent form may also be stamped generating a label for the surgical record (or printing directly on the record) containing both the surgeon and patient I.D.'s, the surgical procedure that is about to take place, the date, time and whatever other data may be required by the institution or by third-party payers and accrediting agencies.

Blood banking poses a particularly acute problem because of the strict regulations normally surrounding blood transfusions. Here the audit trail must be preserved from the blood donor, through typing and testing for infectious agents in the donor blood, through the transfusion requisition, through typing, screening and cross-matching with the recipient's blood, and finally through the transfusion process. All institutions require that the individuals responsible for every step of this procedure be identified and properly authorized.

To provide for a complete audit trail in a blood bank environment, one may begin with a fingerprint storage assembly at the donor site, arranged to accept only dual fingerprint I.D.'s, from the donor and the healthcare professional responsible for doing the venipuncture and drawing the blood. The label produced at this point by the label printer (or a tag stamped by an automatic stamping device) is then affixed to the blood bag. Subsequently, the technician who types and tests the blood in the laboratory will add his or her fingerprint I.D. to the laboratory report card, which is also affixed to the blood bag prior to storage. When a transfusion requisition is prepared, the ordering physician "signs" the requisition via a fingerprint I.D., a blood sample is drawn from the patient for typing, screening and cross-matching, the sample being similarly labeled as described earlier, as are the type and screen and type and cross-matching reports, all of which are affixed to the blood bag. Finally, when the transfusion is administered, the patient I.D. is confirmed through a fingerprint scan and compared by the system against bar code information on the patient sample that had been previously drawn, as well as against bar code data on the blood bag labels for positive confirmation that the proper blood is about to be transfused. These bar codes may be read by portable light pen scanners at the bedside. The staff member handling the transfusion then adds his or her fingerprint I.D. to the transfusion report, thereby completing the audit trail.

A further embodiment of the invention has utility in the maternity ward and helps solve the problem of positive mother-infant correlation. Current practice is to place the newborn's footprint shortly after birth on a card bearing the mother's name and hospital I.D. number. In some institutions the mother's fingerprint is also placed on the same card for verification. The present invention eliminates the need for an inked fingerprint of the mother to be made in the delivery room, as well as providing an identification safeguard prior to placement of the infant's footprint on the identity card. In the delivery room the mother's I.D. is established via a label produced from her fingerprint coupled with that of the obstetrician. Two such labels are produced, one to be placed on the identity card and the other on a wristlet or anklet for the newborn. Subsequently, the infant's footprint would be added to the identity card for complete hard-copy verification. At that time the nurse or other healthcare worker must compare the two labels either visually or (preferably) by means of a bar code scanner to ensure a positive correlation.

The embodiments disclosed herein utilize fingerprint scanning devices to match stored fingerprint data with other identifying characteristics of patients and providers. Of course, the invention can be adapted to include other identification sources, such as foot and palm print or retina scanning devices. The data to be stored may be separated into patient data and provider data or may be resident within one common database or file. Such data storage techniques are well-known and should be readily adaptable to meet the teachings of the instant invention. Further, in healthcare establishments having large numbers of patients and providers, the invention may be modified to require more than one print from an individual (e.g., forefinger and middle finger simultaneously), thereby ensuring more accurate identification of patients and providers. Scanners and associated software for reading and processing two or more prints simultaneously or sequentially from the same individual may be provided to reduce the risk of coincidental matches, i.e. apparent print matches obtained from different individuals.

Thus, the examples shown above are not intended to be all-inclusive. From these examples it should be clear that the invention may be adapted to a wide variety of usages requiring positive identification of patients, patient samples, healthcare providers and services performed for patients; that is, how to establish complete audit trails in a healthcare environment for good medical practice and possible medical-legal purposes.

Thus, although the invention has been described in detail herein, it should be understood that the invention is not limited to the embodiments herein disclosed, but should be interpreted only in accordance with the claims which follow.

What is claimed is:

1. An identification system, comprising:
   first means for obtaining live print indicia from a patient and a second individual;
   controller means for storing said live print indicia from said patient and said second individual;
   second means for obtaining live print indicia directly from a first person to receive treatment and a second person;
   means for comparing said stored print indicia with said live print indicia taken by said second means; and
   means responsive to said comparing means for producing a device comprising a dimensionally stable base member having affixed thereto identification information corresponding to the stored print indicia of said patient or said second individual identifying said patient or said second individual or both, said means for producing being operative to produce said device following a determination by said comparison means that (1) identity between said patient and the first person and between said second individual and the second person has been confirmed and (2) that a relationship exists between the first person and the second person.

2. An identification system as recited in claim 1, wherein said live print indicia comprises a fingerprint.

3. An identification system as recited in claim 1, wherein at least a portion of said identification information affixed to said device is a machine-readable bar code.

4. An identification system as recited in claim 1, wherein said device comprises a label having a printable side and an adhesive side.

5. An identification system as recited in claim 1, wherein said means responsive to said comparing means for producing a device includes means for printing identification information directly onto a form inserted therein.

6. An identification system as recited in claim 1, wherein said second individual is a healthcare provider and said controller means includes stored healthcare provider authorization information associated with said healthcare provider, wherein said device comprising a dimensionally stable base member will be produced only upon indication by said authorization information that the healthcare provider is authorized to perform a given procedure upon said patient.

7. An identification system as recited in claim 1, wherein said controller means includes stored treatment information associated with a patient.

8. An identification system as recited in claim 1, wherein said second individual is a healthcare provider and said controller means stores healthcare provider identification information for all healthcare providers associated with said patient.

9. An identification system as recited in claim 1, wherein said storage means further includes patient and healthcare provider identification information associated with said live print indicia.

10. An identification system as recited in claim 1, wherein at least a portion of said identification information affixed to said device is a visually readable print.

11. An identification system, comprising:
    means for scanning live print indicia directly from first and second related or associated individuals and electronically encoding same;
    a memory device containing stored print indicia and identification information associated with said stored print indicia for said first and second related or associated individuals;

computer/interface means linked to said optical scanner for comparing said electronically encoded live print indicia from said first and second related or associated individuals with said stored print indicia to determine the identity of said first and second related or associated individuals whose prints were scanned; and print generating means linked to said computer/interface means for printing said identification information associated with said stored print indicia on a record medium, said computer/interface means signaling said print generating means to print said identification information only when a positive identification is detected by said computer/interface means.

12. An identification system as recited in claim 11, wherein at least a portion of said identification information affixed to said record medium is a machine-readable bar code.

13. An identification system as recited in claim 11, wherein said device comprises a label having a printable side and an adhesive side.

14. An identification system as recited in claim 4, wherein said means responsive to said comparing means for producing a device includes means for printing identification information directly onto a form inserted therein.

* * * * *

UNITED STATES PATENT AND TRADEMARK OFFICE
CERTIFICATE OF CORRECTION

PATENT NO. : 5,193,855

DATED : March 16, 1993

INVENTOR(S) : Morris H. Shamos

It is certified that error appears in the above-indentified patent and that said Letters Patent is hereby corrected as shown below:

In Column 1, line 32, delete "of" and insert therefor -- or --.

In Column 6, line 22, delete "On" and insert therefor -- on --;

In Column 6, line 64, delete "at" and insert therefor -- as --.

In Fig. 2C, delete "Pm" and insert therefor -- pm --. Therefore, Fig. 2C should appear as follows:

FIG. 2C

Signed and Sealed this

Twenty-eighth Day of June, 1994

Attest:

BRUCE LEHMAN

Attesting Officer

Commissioner of Patents and Trademarks